United States Patent [19]

Gold

[11] 4,110,437

[45] Aug. 29, 1978

[54] METHOD OF TREATING CANCEROUS CACHEXIA IN HUMANS WITH HYDRAZINE SULFATE

[76] Inventor: Joseph Gold, 127 Edgemont Dr., Syracuse, N.Y. 13214

[21] Appl. No.: 765,362

[22] Filed: Feb. 3, 1977

Related U.S. Application Data

[60] Continuation-in-part of Ser. No. 558,255, Mar. 14, 1975, abandoned, which is a continuation of Ser. No. 413,036, Nov. 5, 1973, abandoned, which is a division of Ser. No. 372,097, Jun. 21, 1973, abandoned, which is a continuation-in-part of Ser. No. 198,995, Sep. 15, 1971, abandoned, which is a continuation-in-part of Ser. No. 861,176, Sep. 25, 1969, abandoned.

[51] Int. Cl.$^2$ ............................................. A61K 33/02

[52] U.S. Cl. .................................................. 424/166
[58] Field of Search ........................................ 424/166

[56] References Cited

PUBLICATIONS

Weitzel et al., Z. Physiol. Chem., 348, pp. 433–442, (1967).

*Primary Examiner*—Jerome D. Goldberg
*Attorney, Agent, or Firm*—Henry P. Stevens

[57] ABSTRACT

Hydrazine sulfate alone or formulated with liquid or solid carriers will retard and reduce cancerous cachexia even in the absence of tumor reduction when administered to humans either orally or parenterally.

6 Claims, No Drawings

METHOD OF TREATING CANCEROUS CACHEXIA IN HUMANS WITH HYDRAZINE SULFATE

CROSS REFERENCE TO RELATED APPLICATIONS

This application is a continuation-in-part of U.S. Ser. No. 558,255 filed Mar. 14, 1975 now abandoned, which in turn was a continuation of U.S. Ser. No. 413,036 filed Nov. 5, 1973 now abandoned which in turn was a division of U.S. Ser. No. 372,097 filed June 21, 1973 now abandoned which in turn was a continuation-in-part of U.S. Ser. No. 198,995 filed Sept. 15, 1971 now abandoned which in turn was a continuation-in-part of U.S. Ser. No. 861,176 filed Sept. 25, 1969 and now abandoned.

BACKGROUND OF THE INVENTION

Many different types of chemical compounds have been used in the past to retard or inhibit various kinds of tumors. Such compounds include insulin, fluorouracil, estrogen, tolbutamide, biguanides and nitrogen mustards. However, the degree of successful therapy to date has been marginal at best so that the search for better and more effective anti-tumor agents especially in humans continues at a feverish pace.

In 1967, Weitzel and co-workers reported in Z. Physiol. Chem. 348, 433–442 that hydrazine acetate and sulfate inhibit in vivo the growth of ascites carcinoma and sarcoma 180 in the mouse and Walker carcinosarcoma in the rat. It is well known that such encouraging results in lower animals cannot be extrapolated to determine what effect the same compounds would have on other tumor types or even on the same tumors in humans. Until now, hydrazine sulfate in particular has never been used to treat cancerous cachexia.

SUMMARY OF THE INVENTION

This invention is predicated upon the discovery that hydrazine sulfate when administered either orally or parenterally in effective, non-toxic amounts to humans afflicted with tumors of the prostate, lung, breast, ovaries, thyroid, pancreas, lymph, cervix or gastrointestinal tract will restore the strength of such patients by reducing the cachexia associated therewith by continuing its use even in the absence of tumor reduction.

DESCRIPTION OF THE PREFERRED EMBODIMENTS

The dosages of hydrazine sulfate employed in the present invention can vary from 2 to 5 mg/kg daily which is well below the $LD_{50}$ dosage and has been found to be well tolerated in the majority of patients so treated. Preferably, the regimen followed is one 60 milligram capsule of hydrazine sulfate daily for the first three days, then two such capsules daily for the next 3 days and three 60 milligram capsules each day thereafter until the patient shows definite signs of improvement. If adequate response is observed on two such capsules daily, the patient should be maintained on this dosage and not increased. In actual practice, patients weighing over 130 pounds do well on four 60 milligram capsules daily whereas patients weighing less than 100 pounds generally respond on a dosage of 30 milligrams administered twice a day.

Hydrazine sulfate is most effective when administered by itself one to two hours before meals in the form of a gelatin capsule. If desired, the sulfate can be dissolved or suspended in sterile, aqueous, isotonic, saline solution and given orally or parenterally. Likewise, hydrazine sulfate can be formulated with solid carriers such as talc, corn starch or stearic acid and compressed into tablets for oral administration. Such tablets can be enteric coated with shellac or cellulose acetate phthalate in a manner well known to those skilled in the pharmaceutical art.

Several patients with tumors of the prostate, lung, breast, ovary, lymph, cervix, thyroid and pancreas were treated with hydrazine sulfate according to the preferred regimen previously set forth. Subjective results observed within a week of such therapy included restoration of vigor and a sense of well being. Objective results included cessation of weight loss and ensuing weight gain plus restoration to normal of abnormal blood chemistries. Although the tumors in these patients did not completely regress, there was a definite, noticeable inhibition in the growth of the tumors within 1 to 3 weeks of therapy. In each instance, the hydrazine sulfate was given daily for several weeks just as insulin is given to a diabetic thus making it possible for the patients to endure their affliction and prolong their lives. Less than 3% of the patients displayed minor side effects including transient gastritis which was quickly relieved by reducing the dosage to about one-half for a few days before reinstituting full dosage. Beneficial effects were likewise observed in the retarding and reducing of cancerous cachexia by continuing the use of hydrazine sulfate even in the absence of tumor reduction in said patients.

What I claim is:

1. A method of retarding and reducing cancerous cachexia in a human so afflicted which comprises internally administering to said human hydrazine sulfate in an effective dosage sufficient to retard and reduce the cachexia and continuing its use in the absence of tumor reduction.

2. A method as in claim 1 in which the hydrazine sulfate is administered orally in dosage form.

3. A method as in claim 2 in which the dosage form is a gelatin capsule.

4. A method as in claim 1 in which the hydrazine sulfate is administered parenterally.

5. A method as in claim 1 in which the dosage of hydrazine sulfate is 2 to 5 mg/kg of body weight daily.

6. A method as in claim 1 in which the hydrazine sulfate is administered in a daily regimen of one 60 milligram capsule for 3 days, then two 60 milligram capsules for the next 3 days and three 60 milligram capsules each day thereafter.

* * * * *

UNITED STATES PATENT AND TRADEMARK OFFICE
CERTIFICATE OF CORRECTION

PATENT NO. : 4,110,437

DATED : August 29, 1978

INVENTOR(S) : Joseph Gold

It is certified that error appears in the above-identified patent and that said Letters Patent are hereby corrected as shown below:

Under column 2, line 46, after the word "use," please insert the word "even".

*Signed and Sealed this*

*Seventh* Day of *April 1981*

[SEAL]

*Attest:*

RENE D. TEGTMEYER

*Attesting Officer*     *Acting Commissioner of Patents and Trademarks*